United States Patent [19]

Jongsma et al.

[11] 4,296,245

[45] Oct. 20, 1981

[54] METHOD FOR THE PREPARATION OF A PURE ALKALI METAL BENZOATE AND BENZYL ALCOHOL

[75] Inventors: Cornelis Jongsma, Oirsbeek; Leon H. B. Frijns, Valkenburg; Paula A. M. Raven-Donners, Sittard, all of Netherlands

[73] Assignee: Stamicarbon, B.V., Geleen, Netherlands

[21] Appl. No.: 150,690

[22] Filed: May 16, 1980

[30] Foreign Application Priority Data

May 17, 1979 [NL] Netherlands .......................... 7903878

[51] Int. Cl.³ ....................... C07C 51/42; C07C 27/04
[52] U.S. Cl. ..................................... 562/494; 568/814
[58] Field of Search ................. 562/487, 494; 568/814

[56] References Cited

U.S. PATENT DOCUMENTS

| | | | |
|---|---|---|---|
| T880,007 | 11/1970 | Paris .................................... | 562/487 |
| 3,642,883 | 2/1972 | Jackson ............................... | 562/487 |
| 4,092,353 | 5/1978 | Wolf ................................... | 562/494 |

FOREIGN PATENT DOCUMENTS 15-12780  6/1940  Japan ................................... 562/494

*Primary Examiner*—Alan Siegel
*Attorney, Agent, or Firm*—Cushman, Darby & Cushman

[57] ABSTRACT

The invention relates to a method for the preparation of a pure alkali metal benzoate, specifically of a pure alkali metal benzoate from benzyl benzoate prepared by oxidation of an alkyl benzene compound, specifically toluene, with a gas containing molecular oxygen, besides benzyl alcohol. Very specifically the invention relates to a method for the preparation of sodium benzoate besides benzyl alcohol.

For this purpose crude benzyl benzoate is subjected to a treatment with a reducing substance to convert impurities, under such circumstance that, in the process, there will be no conversion of any substantial quantity of benzyl benzoate. Subsequently the benzyl benzoate is saponified to the alkali metal benzoate and benzyl alcohol.

26 Claims, No Drawings

METHOD FOR THE PREPARATION OF A PURE ALKALI METAL BENZOATE AND BENZYL ALCOHOL

This invention relates to a method for the preparation of a pure alkali metal benzoate, specifically of a pure alkali metal benzoate from benzyl benzoate prepared via the oxidation of an alkyl benzene compound, specifically toluene, with a molecular oxygen-containing gas, with benzyl alcohol being obtained along therewith. Very specifically the invention relates to a method for the preparation of sodium benzoate, along with benzyl alcohol.

The oxidation reaction may take place either in the liquid phase with, e.g., a cobalt and/or manganese salt that is soluble in the reaction medium as a catalyst, or in the gaseous phase with, e.g., a catalyst based on an oxide of vanadium or another transition metal (Stanford Research Institute (SRI)-reports No. 7 (1965), 29–33 and 38–43; No. 7A (1968), 241–243; No. 7B (1976), 53–55 and 60–62, No. 22 (1967) 113–118 and 124–148, No. 22A (1972), 147–151, No. 22B (1977), 147.

Sodium benzoate is an important substance, which is employed, for instance, as a preservative in the food industry. Such use generally requires a high degree of purity for the sodium benzoate. However, crude sodium benzoate, and specifically sodium benzoate prepared from the oxidation-reaction products of toluene, with a molecular oxygen-containing gas, generally contains cumbersome impurities which are very difficult to remove. Specifically, it is difficult to obtain from such a crude sodium benzoate a product which meets the pharmacopoeia requirements for food grade materials.

The essential purpose of the invention is to provide a solution to this problem.

According to this invention, crude benzyl benzoate, specifically benzyl benzoate obtained from the oxidation of an alkyl benzene compound, specifically toluene, with a molecular oxygen-containing gas is subjected to a treatment with a reducing agent to convert impurities, under such conditions that, in the process, there will be no conversion of any substantial quantity of the benzyl benzoate. This treatment is then preferably followed by a washing with an aqueous akaline solution. Preferably also, the benzyl benzoate is then distilled. Subsequently, the benzyl benzoate is saponified, for instance, with an alkali metal hydroxide solution, to obtain the alkali metal benzoate and benzyl alcohol.

From the resulting solution the benzyl alcohol can then be extracted with, e.g., an organic extractant, such as toluene, and this alcohol can subsequently be recovered by distillation. The alkali metal benzoate can itself be recovered by e.g., evaporation of the aqueous solution thus obtained. Preferably, this solution is cleaned, prior to this evaporation, of residues of toluene, benzyl alcohol, etc., by e.g., steam distillation.

The alkali metal benzoate thereby obtained, and specifically the sodium benzoate, meets the said pharamacopoeia requirements. As far as sodium benzoate is concerned, this means that, after drying to constant weight, the product must be capable, in each of the following tests, of achieving the following results:

| | | |
|---|---|---|
| 1. | Acidity/alkalinity | 2g dissolved in water must not require more than 0.05–0.15 ml 0.1 N aqueous NaOH/HCl for neutralization (indicator: phenolphthalein). |
| 2. | KMnO₄ number | sodium benzoate in acid medium must not require more than 0.5 ml 0.1 N KMnO₄. |
| 3. | Content | The percentage by weight of sodium benzoate must be at least 99.5%. |
| 4. | Color | A solution of 10 g in 100 ml H₂O must be of a lighter color than or of the same color as a solution in 100 ml 1 N aqueous sulphuric acid of 4 ml color standard as described in Nederlandse Farmacopee VI. |
| 5. | Turbidity | A solution of 10 g in 100 ml H₂O must be clearer than a suspension in 100 ml H₂O of 1 ml standard suspension of Bolus Alba as described in Nederlandse Farmacopee VI. |
| 6. | H₂SO₄ test | The color of 0.5g sodium benzoate mixed with 5 ml concentrated H₂SO₄ must, after 15 minutes, not be more intense than the standard solution "Matching Fluid Q" (MFQ) as described in US Pharmacopoeia XIX. |

Suitable reducing substances that can be used in applying the method of this invention include hydrogen, which is preferably used in the presence of a suitable hydrogenation catalyst, and those metals with reducing properties from the Groups IA, IIA, IIB, IIIA, IVA, VIIB and VIII of the Periodic System, e.g., magnesium, calcium and in particular zinc, iron and aluminum—which metals are used in the presence of water, e.g. by contacting them in the form of an aqueous suspension with the benzyl benzoate.

Suitable hydrogenation catalysts in the treatment of the benzyl benzoate with hydrogen are the well known hydrogenation catalysts, e.g. those based on metals from Group VIII of the Periodic System, e.g., palladium, nickel, platinum, iridium or rhodium. The said catalytic material may be employed on a carrier, e.g., carbon, aluminum oxide, silica or titanium oxide. Particularly suitable as such a catalyst are Raney nickel and palladium-on-carbon. Preferably, the catalysts are used in quantities of from 1 to 100 mg-atom of active substance per kg benzyl benzoate, and specifically in quantities of about 2 to 50 mg atom of active substance per kg benzyl benzoate.

In applying the method according to the invention generally 2 to 15 N liters of hydrogen is taken up per kg benzyl benzoate, per hour. Often, from 5 to 10 N liters of hydrogen per kg benzyl benzoate is taken up, per hour. The benzyl benzoate can be brought into contact with the hydrogen in different ways. For example, the benzyl benzoate can be stirred in a hydrogen atmosphere for a certain length of time, or the hydrogen can be bubbled through the benzyl benzoate or be passed over it. The duration of the treatment of the benzyl benzoate with hydrogen is generally between about 0.25 and 5 hours, preferably between about 0.5 and 1.5 hours. The use of larger quantities of catalyst, or of a large excess of hydrogen, and/or an extension of the duration of the treatment are not excluded, but offer no advantages. This hydrogen treatment of the crude benzyl benzoate is also preferably effected at a mild temperature in order to suppress hydrogenation of the benzyl benzoate. By a "mild temperature" there is here meant a temperature at which the impurities are, but the benzyl benzoate is not, substantially hydrogenated. A suitable temperature range is from 290 to 380 K. Particularly suitable are temperatures of between about 320 and 360 K. The reaction pressure is itself not critical so long as the liquid phase is maintained. Suitable reaction pressures are, for instance, between about 100 and 1000 kPa, specifically between about 200 and 500 kPa.

In the reduction treatment of the benzyl benzoate using the above-identified metals having reducing properties, these metals are generally consumed in quantities of between about 5 and 30 mg atom per kg benzyl benzoate, often in quantities of between about 10 and 20 mg atom per kg benzyl benzoate. A suitable temperature range for this treatment of benzyl benzoate is from the freezing point of the water under the reaction conditions (about 270 K.) up to about 380 K., specifically from about 275 to 360 K. Temperatures higher than 380 K. can be employed, if desired. The duration of the treatment is usually between 0.1 and 5 hours, and preferably between about 0.5 and 3 hours. Suitable quantities of water during this treatment are from about 1 to 1000 g per kg benzyl benzoate. Particularly suitable are quantities of about 20 to 500 g water per kg benzyl benzoate. The reaction pressure is not itself critical but should be such that a liquid phase is maintained. Suitable reaction pressures are thus between about 50 and 300 kPa, specifically between about 75 and 200 kPa.

In order to shorten the time and/or to lower the temperature required for the treatment, a base can be incorporated in the aqeuous reaction medium. If, in this process, a sufficiently strong alkaline solution, for instance from 2 to 6 N is used, then the washing with an aqueous alkaline solution after the "metal-base" treatment, is virtually superfluous. Suitable bases are the water-soluble inorganic bases, e.g., hydroxides of alkali metals and alkaline earth metals, the alkali metal carbonates and hydrogen carbonates, and also ammonia, or water-soluble organic bases, e.g., water-soluble amines. Particularly suitable are the hydroxides and carbonates of sodium and potassium, and calcium hydroxide. Suitable quantities of base are up to 2500 mmol per kg benzyl benzoate, specifically to 1500 mmol per kg benzyl benzoate. The quantity of base is calculated as the equivalent quantity of NaOH.

Suitable aqueous alkaline solutions for the subsequent washing of the treated benzyl benzoate include, among others, aqueous solutions of hydroxides of alkali metals and earth alkaline metals, alkali metal carbonates and hydrogen carbonates, and ammonia or water-soluble organic bases such as amines. Particularly suitable are aqueous solutions of hydroxides or carbonates of sodium or potassium, and calcium hydroxide. In these washings, quantities of solution of 0.1 to 0.5 liter per kg benzyl benzoate having a concentration of 2 to 6 N are often used. The washing may generally be done at a temperature between the freezing point of the water under the prevailing conditions (about 270 K.) and up to 330 K., and at a pressure of 50 to 200 kPa. Instead of washing with an aqueous alkaline solution, the treated benzyl benzoate can instead be passed over a basic ion exchanger resin, with which virtually the same results are achieved.

The distillation of the treated benzyl benzoate can be carried out under reduced or atmospheric or elevated pressure, i.e., at a pressure of 0.5 to 5 kPa. A reduced pressure is preferred.

A saponification of the benzyl benzoate is carried out with the respective alkali metal hydroxide and/or suitable salts, e.g., sodium carbonate, potassium carbonate. Particularly suitable are aqueous solutions of preferably 2 to 4 N concentration. The saponification is generally carried out at a temperature of between 350 and 400 K. and a pressure of 100 to 200 kPa.

According to another suitable mode of practicing the method according to the invention, a mixture of the impure benzyl benzoate and water, optionally containing a base, is passed over a bed of solid metal particles. Particularly suitable for this purpose is a bed of zinc dust. No metal particles need then be separated, after the treatment, from the reaction mixture. Advantages of this procedure are the long on-stream time of the equipment now possible owing to the very slow exhaustion of the material present.

The invention will now be further elucidated by reference to the following non-restrictive examples and to the comparative experiment.

EXAMPLE I 75 g of crude benzyl benzoate, which had been prepared by oxidation of toluene with a gas containing molecular oxygen in the liquid phase with a cobalt catalyst, and 0.375 g palladium-on-carbon (5% by weight of Pd), was heated in a reaction vessel of 500 ml at 323 K. for 1.5 hours in the presence of hydrogen while being well shaken. The initial pressure was 445 kPa. After the treatment the pressure had fallen to 245 kPa. After the catalyst had been filtered off, the product was distilled. The main distillate fraction was subsequently washed with cold 3 N aqueous NaOH. After removal of this alkaline water layer, the remaining benzyl benzoate was saponified with aqueous NaOH to sodium benzoate and benzyl alcohol. From the resulting solution benzyl alcohol was extracted with toluene. The sodium benzoate was recovered by evaporation of the aqueous solution. Before the evaporation, this solution had been cleaned out of residues of toluene, benzyl alcohol, etc., by steam distillation. The sodium benzoate obtained was found, in the tests described above, to meet all the stated requirements.

EXAMPLE II 150 g crude benzyl benzoate, prepared in the same way as described in Example I, and 75 ml water and 5 g zinc granules were heated for 1 hour at 353 to 358 K. at atmospheric pressure, while being stirred. After this treatment, the reaction mixture was cooled down and the zinc granules were separated out. After that the water layer was separated off. Subsequently, the benzyl benzoate was washed with 75 ml 3 N aqueous NaOH at a temperature of 278 to 283 K. After removal of this alkaline water layer the remaining benzyl benzoate was distilled. The main fraction was subsequently saponified with aqueous NaOH to sodium benzoate and benzyl alcohol. From the resulting solution benzyl alcohol was extracted by means of toluene. The sodium benzoate was recovered from the aqueous solution in the same way as in Example I. The sodium benzoate so obtained was found, in the tests described above, to meet all the stated requirements.

EXAMPLE III 120 g crude benzyl benzoate, prepared in the same way as described in Example I, and 12 ml 6 N aqueous NaOH and 4 g zinc granules, were heated at 313 K. for 2.5 hours at atmospheric pressure, while being well stirred. After the alkaline water layer and the zinc had been separated out, the benzyl benzoate was distilled. The main fraction was subsequently saponified with aqueous NaOH to sodium benzoate and benzyl alcohol. From the resulting solution benzyl alcohol was extracted with toluene. The sodium benzoate was recovered from the aqueous solution in the same way as in Example I. The sodium benzoate obtained was found, in the tests described above, to meet all the stated requirements.

EXAMPLE IV 200 g crude benzyl benzoate, prepared in the same way as described in Example I, and 1.37 g aluminium powder, were cooled at 278 to 283 K. With good stirring, 90 ml 3 N aqueous NaOH was added in drops. The temperature was maintained at 278 to 283 K. The experiment was done at atmospheric pressure. After 0.5 hours the aluminum and the aqueous alkaline layer were separated out. After that the benzyl benzoate was distilled. The main fraction was subsequently saponified with aqueous NaOH to sodium benzoate and benzyl alcohol. From the resulting solution benzyl alcohol was extracted with toluene. The sodium benzoate was recovered from the aqueous solution in the same way as in Example I. The sodium benzoate obtained was found, in the tests described above, to meet all the stated requirements.

COMPARATIVE EXPERIMENT 106 g crude benzyl benzoate which had been prepared in the same way as described in Example I was saponified with aqueous NaOH to sodium benzoate and benzyl alcohol. From the resulting solution benzyl alcohol was extracted by means of toluene. The sodium benzoate was recovered from the aqueous solution in the same way as in Example I. The sodium benzoate obtained was found, in the tests described above, unsatisfactory and incapable of meeting the stated requirements except only for the acidity/alkalinity test.

What is claimed is:

1. A method for the preparation of a food-grade pure alkali metal benzoate from crude benzyl benzoate, obtained by the oxidation of an alkylbenzene compound with a gas containing molecular oxygen, wherein said crude material is subjected to treatment with a reducing substance,
    selected from the class of (a) hydrogen or (b) the metals with reducing properties in groups IA, IIA, IIB, IIIA, IVA, VIIB, and VIII of the periodic system in the presence of water, to convert impurities therein to alkaline-aqueous soluble components without substantial conversion of any benzyl benzoate, and subsequently saponifying said benzoate to obtain said food-grade pure alkali metal benzoate.

2. Method according to claim 1, wherein said alkylbenzene is toluene.

3. Method according to claim 1, wherein when hydrogen is used as the reducing substance said method is carried out in the presence of a hydrogenation catalyst.

4. Method according to claim 3, wherein the catalyst is a metal from Group VIII of the Periodic System.

5. Method according to claim 4, wherein Raney nickel is used.

6. Method according to claim 4, wherein palladium-on-carbon is used as said catalyst.

7. Method according to claims 1 or 2, wherein said metal is zinc.

8. Method according to claims 1 or 2, wherein said metal is iron.

9. Method according to claims 1 or 2, wherein said metal is aluminum.

10. Method according to claims 1 or 2, wherein the metal is employed as an aqueous suspension.

11. Method according to claims 1 or 2, wherein a base is incorporated in said water.

12. Method according to claim 11, wherein sodium, potassium and/or calcium hydroxide is used as said base.

13. Method according to claim 11, wherein sodium and/or potassium carbonate is used as said base.

14. Method according to claims 1 or 2, wherein a mixture of the impure benzyl benzoate and water, is passed over a bed of solid particles of said metal.

15. Method according to claim 14, wherein said bed of solid particles is zinc dust.

16. Method according to any one of claims 1 or 2, wherein the reduction-treated benzyl benzoate is subsequently washed with an aqueous alkaline solution.

17. Method according to claim 16, wherein sodium, potassium and/or calcium hydroxide is used as said aqueous alkaline solution.

18. Method according to claim 16, wherein sodium and/or potassium carbonate is used as said aqueous alkaline solution.

19. Method according to any one of claims 1 or 2, wherein the treated benzyl benzoate is subsequently distilled.

20. Method according to any one of claims 1 or 2, wherein said alkali metal is sodium.

21. Method according to any one of claims 1 or 2, wherein benzyl alcohol is recovered from the saponified reaction mixture.

22. Method according to claim 21, wherein said benzyl alcohol is distilled from the extract formed by subjecting the saponified reaction mixture, to an extraction with an organic extractant.

23. Method according to claim 22, wherein toluene is used as said organic extractant.

24. Method according to any one of claims 1, 2, or 22, wherein the saponified reaction mixture is cleaned of organic residues.

25. Method according to claim 24, wherein said cleaning is effected by steam distillation.

26. Method according to claim 1, wherein the said benzyl benzoate is prepared by oxidation of the said alkyl benzene with a gas containing molecular oxygen in the liquid phase with a cobalt catalyst.

* * * * *

UNITED STATES PATENT AND TRADEMARK OFFICE
CERTIFICATE OF CORRECTION

PATENT NO. : 4,296,245
DATED : October 20, 1981
INVENTOR(S) : Cornelis Jongsma, Leon H. B. Frijns, Paula A. M. Raven-Donners It is certified that error appears in the above—identified patent and that said Letters Patent is hereby corrected as shown below:

Cover sheet, Foreign Application Priority Data, Netherlands "7903878" should read --7903876--

Signed and Sealed this

Twenty-third Day of February 1982

[SEAL]

Attest:

GERALD J. MOSSINGHOFF

Attesting Officer   Commissioner of Patents and Trademarks